(12) United States Patent
Sainty

(10) Patent No.: US 7,183,772 B1
(45) Date of Patent: Feb. 27, 2007

(54) ION DETECTOR

(75) Inventor: Wayne G. Sainty, Sydney (AU)

(73) Assignee: Saintech Pty Ltd, Sydney (AU)

( * ) Notice: Subject to any disclaimer, the term of this patent is extended or adjusted under 35 U.S.C. 154(b) by 0 days.

(21) Appl. No.: 11/287,092

(22) Filed: Nov. 28, 2005

(30) Foreign Application Priority Data

Sep. 30, 2005 (AU) .............................. 2005905400

(51) Int. Cl.
*G01N 27/662* (2006.01)
*G01N 27/66* (2006.01)

(52) U.S. Cl. ...................................... 324/459; 324/457

(58) Field of Classification Search ................ 324/459, 324/465, 458, 72
See application file for complete search history.

(56) References Cited

U.S. PATENT DOCUMENTS

| | | | | |
|---|---|---|---|---|
| 2,619,836 A | * | 12/1952 | Downing ................. 73/861.05 |
| 3,812,419 A | * | 5/1974 | Kaunzinger et al. ........ 324/458 |
| 3,824,454 A | * | 7/1974 | Stern et al. ................. 324/457 |
| 3,887,877 A | * | 6/1975 | Vosteen ....................... 330/10 |
| 4,056,772 A | * | 11/1977 | Graf von Berckheim ..... 324/72 |
| 4,366,438 A | * | 12/1982 | Ibe et al. ..................... 324/468 |
| 4,775,838 A | * | 10/1988 | Mizuta et al. .............. 324/468 |
| 4,973,910 A | * | 11/1990 | Wilson ....................... 324/457 |
| 5,591,969 A | * | 1/1997 | Park et al. .................. 250/287 |
| 6,031,378 A | * | 2/2000 | Rosin ......................... 324/452 |
| 2005/0127890 A1 | * | 6/2005 | Swenson et al. .............. 324/72 |

* cited by examiner

*Primary Examiner*—Anjan Deb
(74) *Attorney, Agent, or Firm*—Darren Gardner

(57) ABSTRACT

A charge detector includes an outer housing having an entrance aperture. Within the housing is disposed a charge capture element that is electrically isolated from the outer housing. The charge capture element includes a plurality of apertures, such as provided by a mesh, and a conductive surface facing substantially away from the entrance aperture.

18 Claims, 4 Drawing Sheets

ION DETECTOR

FIELD OF THE INVENTION

This invention relates to detectors for measuring the flux of charged particles over a surface area. The invention was conceived in the context of a thin film process known as Ion Assisted Deposition (IAD) and has particular relevance thereto, however it will be understood by the skilled addressee that many other applications of the invention are possible.

BACKGROUND OF THE INVENTION

Ion assisted deposition is a process for the creation of thin films in which a substrate is simultaneously, or nearly simultaneously, bombarded by a flux of evaporant material that forms the thin film and a flux of ions that enhances the thin film properties. The role of the ions can be to provide an additional source of energy, eg for densifying the growing film and for modifying the physical properties of the film such as the optical properties, hardness and the like. Alternatively or in addition, the ions may be used to modify the chemical properties of the film by reacting with the film, such as in the conversion of metal films to oxides or nitrides.

In all of these processes, it is important to know the rate of arrival of ions at the substrate in relation to the rate of arrival of evaporant material, known as the ion to atom arrival ratio. Here, the term atom is used loosely as it also covers the situation where molecules of evaporant are being deposited.

A problem that exists in the thin film industry is that it is difficult to measure the ion current during deposition because the detector has to be placed not only in the path of the ions, but also the evaporant. Because the evaporant is most commonly a dielectric material or a metal that is converted to a dielectric by ion bombardment, an insulating layer is formed on the detector that prevents further ions from being properly detected.

It is therefore an object of the present invention to provide a detector that can accurately measure a charged particle flux during a thin film deposition process.

SUMMARY OF THE INVENTION

In a first aspect, the invention provides a charge detector including an outer housing including an entrance aperture, the detector further including a charge capture element disposed within said outer housing and electrically isolated from said outer housing, wherein said charge capture element includes a plurality of apertures and a conductive surface facing substantially away from said entrance aperture.

Preferably the charge detector includes an electrical contact electrically connected to said conductive surface of said charge capture element and extending from said charge capture element through said housing, said electrical contact being electrically isolated from the housing.

Preferably the charge detector includes a signal line extending from said electrical contact for conducting a current signal. Preferably the signal line includes at least one inner signal line and an outer electrical shield separated from said at least one inner signal line by an insulator. Preferably the signal line is further adapted to conduct a voltage to said detector surface.

In one embodiment the housing is provided with an electrical contact point.

In a further aspect, the invention provides a charge detector system including:— a charge detector including an outer housing including an entrance aperture, a charge capture element disposed within said outer housing, an electrical contact electrically connected to said charge capture element and extending from said charge capture element through said housing, said charge capture element and said electrical contact being electrically isolated from said housing, wherein said charge capture element includes a plurality of apertures and a conductive surface facing substantially away from said entrance aperture; said system further including:— a signal line; and a control circuit;

wherein the signal line extends from said charge detector to said control circuit, wherein the control circuit is adapted to measure a signal in said signal line and to provide an output signal indicative of a charge captured by said charge capture surface.

In one embodiment, the control circuit provides the output signal to a visual display.

Preferably the output signal indicative of the charge captured by said charge capture surface is a current signal.

Preferably the control circuit includes an RMS converter for converting a time varying signal to an RMS signal.

Preferably the control circuit includes a bias circuit for providing a bias voltage to said charge capture surface. Preferably the bias voltage is provided to the charge capture surface through the signal line.

Preferably the control circuit includes a signal amplifier for amplifying the signal received from the charge detector.

In a preferred embodiment, the system includes a temperature sensor, the signal line including at least one line for conducting a temperature indicating signal from said temperature sensor to said control circuitry. Preferably the signal line includes a temperature sensor in thermal contact with said charge detector for measuring the temperature of said charge detector. Preferably the signal line includes a thermocouple at an end of said signal line connected to said charge detector. Preferably the control circuitry includes switching circuitry for switching between a charge measuring mode and a temperature measuring mode. Preferably the control circuitry removes a bias voltage from said signal line during said temperature measuring mode.

BRIEF DESCRIPTION OF THE DRAWINGS

The invention will now be described by way of example only with reference to preferred embodiments and to the accompanying drawings in which.

DETAILED DESCRIPTION OF PREFERRED EMBODIMENTS

Figure 1:
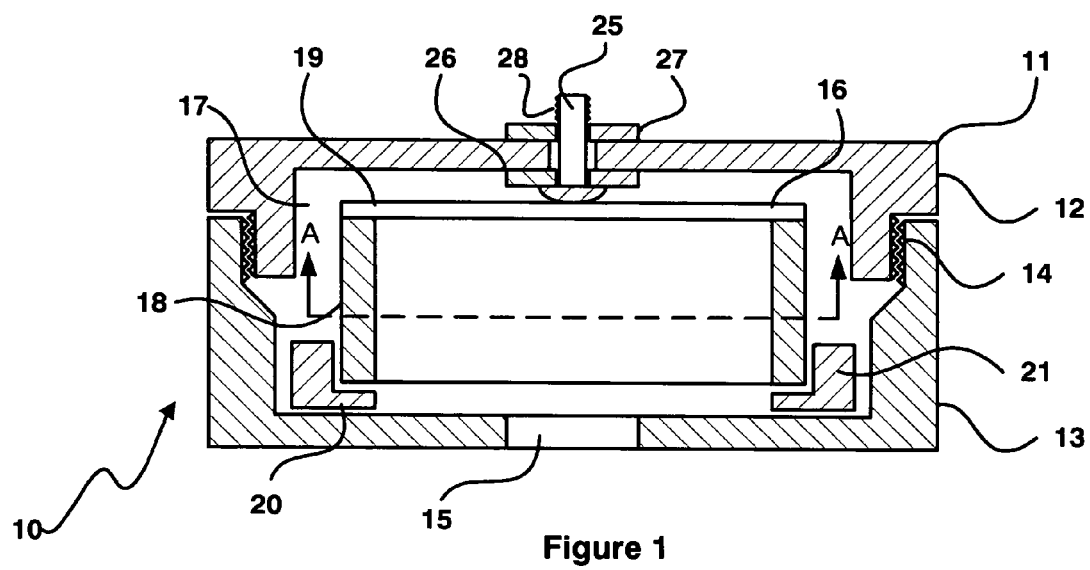
FIG. 1 shows a cross section through a detector in accordance with the invention.
Figure 2:
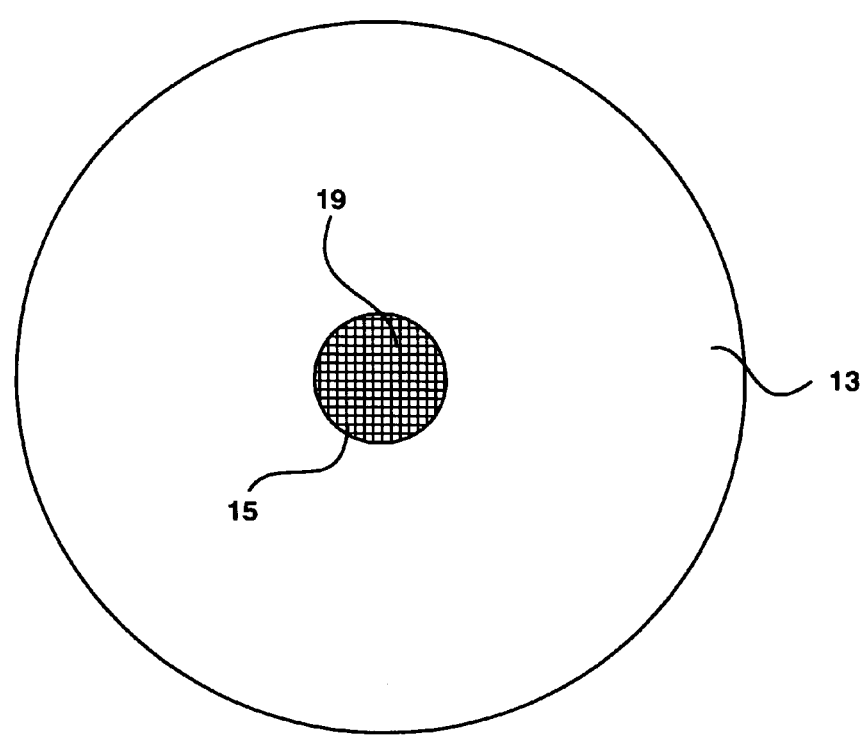
FIG. 2 shows an end view of the detector of FIG. 1.
Figure 3:
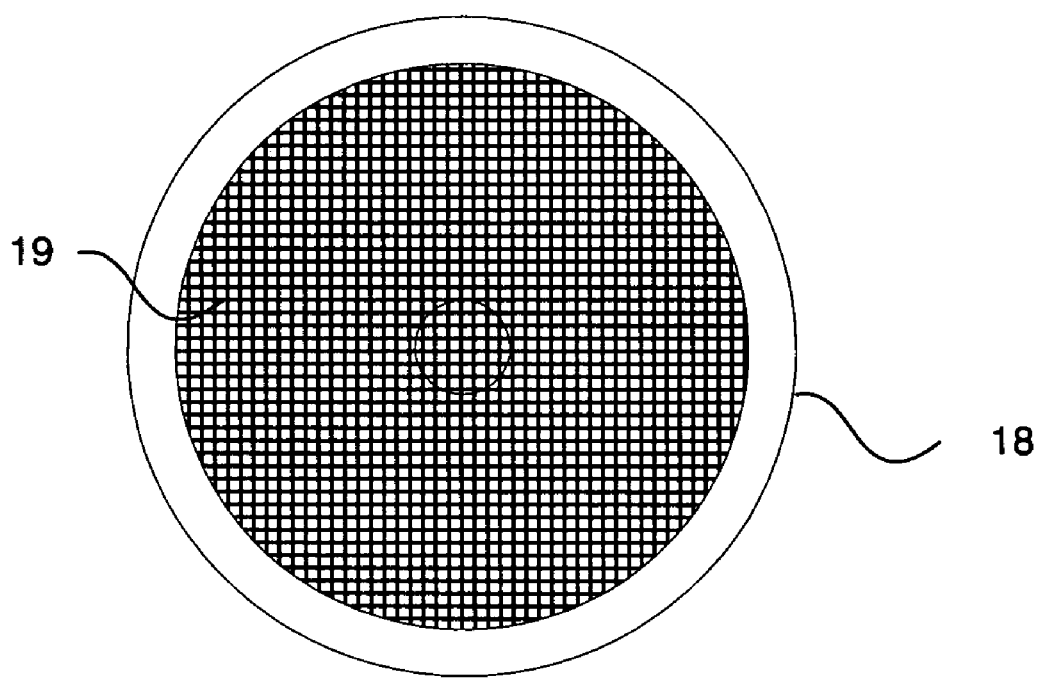
FIG. 3 shows the charge capture element through section A—A of FIG. 1.

With reference firstly to FIGS. 1 and 2, a charge detector is shown generally at 10 having a two part outer housing 11 formed from a base housing piece 12 and a cap housing piece 13 that engage each other through a screw thread 14. The cap 13 has an entrance aperture 15 that provides an entry point for charged particles into an internal cavity 17 of the housing. Within the housing there is provided a charge capture element 16. FIG. 3, which provides a cross section of the charge capture element through line A—A shows the charge capture element in more detail. The element includes a hollow tube 18, for example of stainless steel. The tube is approximately 10 mm in length and has a wall thickness of approximately 1 mm. Closing one end of the tube is a conductive mesh 19, preferably also of stainless steel, which may be welded, clamped or otherwise affixed to the tube.

The charge capture element 16 is held within the housing by an annular insulator 20 that caps the end of the tube 18 between the element 16 and the housing 11. The insulator 20 includes a side flange 21 that acts to locate the element 16 radially within the cavity 17 of the housing 11.

The charge capture element 16 is further located within the cavity 17 by an electrical contact 25, which may be a screw or similar piece. The contact 25 extends through the base housing element 12 and is electrically isolated from the housing by inner and outer insulators 26,27 respectively. A screw thread 28 at the exposed end of the contact 25 provides a simple means for connecting a signal line to be described later. Any alternative connection known to the skilled address, such as a BNC connector may be used.

When completely assembled, the electrical contact 25 engages the mesh 19, thereby forming an electrical path between the charge capture element and the contact 25. A sealing cap (not shown) may be provided around the contact 25 to prevent any charge particles from traveling around the detector and being detected at the contact.

Figure 4:
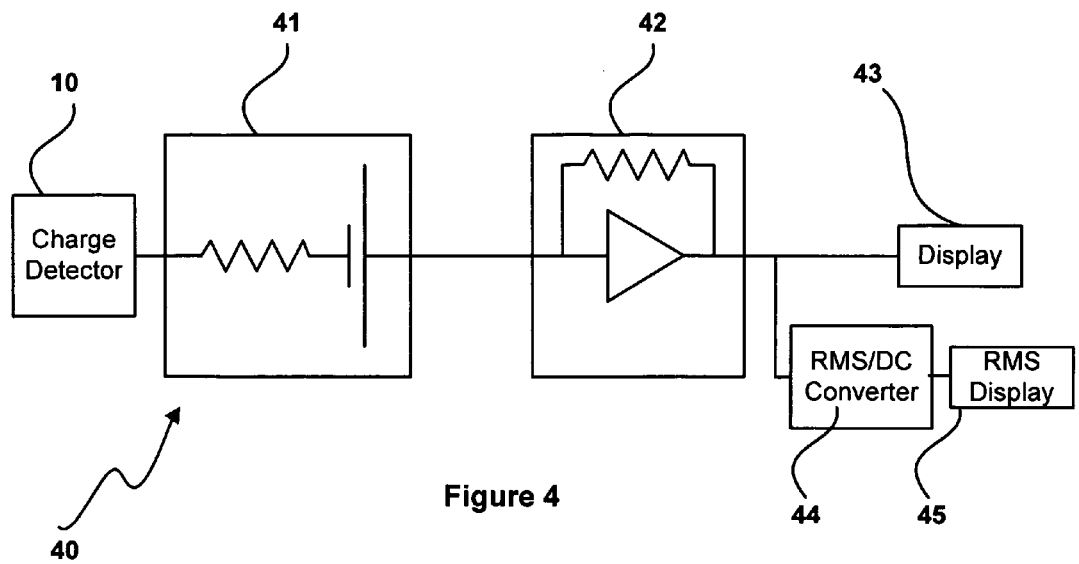
FIG. 4 shows an example of a control circuit for use with the detector.

The ion current detector has been primarily designed for use with ion assistance ion sources, such as gridless, end-Hall or cold cathode ion sources. Such devices produce a beam of positive ions with the beam being charge neutralized by the addition of electrons from a neutralizer, filament or similar. Because the ion beam is charge neutral, in order to produce a meaningful reading the charge capture element of the detector must be biased to discriminate between the ions and electrons. To this end, the ion detector is operated in conjunction with a control circuit, one preferred embodiment of which is shown in FIG. 4.

The circuit 40 includes a bias circuit 41 that provides a bias voltage to the charge capture element of the detector 10. For measuring positive ions, a typical bias voltage would fall in the range between −10 and −80 volts. In this embodiment, the positive side of the bias circuit connects to the earth of the vacuum chamber to provide a return path for the charges measured by the detector. The return path passes through a charge amplifier circuit 42 which outputs a real time voltage signal to a display 43, the voltage signal being proportional to the current/charge captured by the detector.

Charges collected by the charge capture element are conducted as an electrical current to the amplifier circuit which then provides an indication of the current on the display.

As some ion sources now commercially available operate using non-DC principles, the control circuit 40 also includes an RMS to DC converter 44 that outputs to a second display 44 a DC signal indicating the RMS current measured by the detector.

Figure 5:
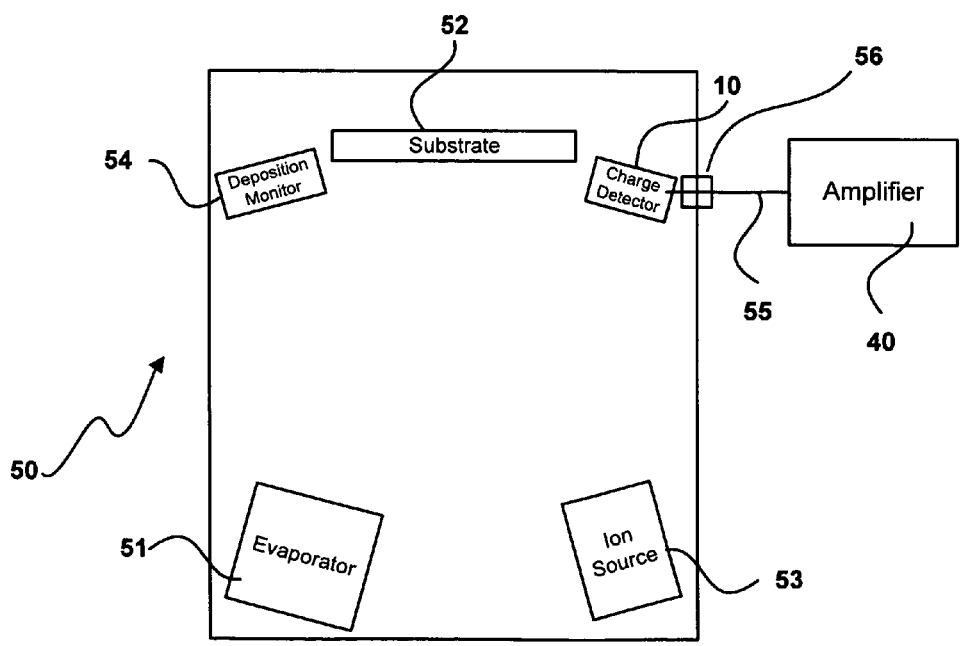
FIG. 5 shows the detector and control circuit used in a deposition environment.

Referring now to FIG. 5, there is shown the ion current detector in situ in a vacuum deposition chamber. The chamber 50 has typical deposition apparatus disposed within it such as an electron beam or thermal evaporator 51 which creates the evaporant material, a substrate 52 on which is formed a thin film of the evaporant and an ion source 53 for ion assisting the film formed on the substrate. In a typical arrangement, a deposition monitor, such as a quartz crystal monitor 54, would be disposed to measure the arrival rate of evaporant at the substrate. In an ion assisted deposition process, it is equally important to measure the arrival rate of ions from the ion source, in order to gauge the amount of ion assistance that the thin film receives. Thus, an ion detector 10 in accordance with the invention is also disposed within the chamber and placed in the path of the ion beam. The control circuit 40 connects to the ion detector 10 along a signal line 55 that passes through an electrical feedthrough 56 of the vacuum chamber.

The housing of the detector is preferably mounted such that it is earthed to a suitable reference point. However, in some applications an insulating mounting may be used, in which case the detector may be provided with an electrical contact point which provides a convenient contact point for providing the housing with an earth potential or any other potential that may be required depending on the application.

The detector operates on the principle that the evaporant material follows a substantially line of sight trajectory whilst the ions are able to follow curved trajectories caused by electric field perturbations. The surface of the mesh facing the entrance aperture will be exposed to a build up of dielectric evaporant material and will eventually become non-conducting. The rear surface of the mesh however will remain uncoated and, being electrically biased, will be attractive to any charged particles. With these charge particles able to pass through the apertures in the mesh, the charged particles can be properly detected. It will of course be understood by the skilled addressee that the mesh may be replaced with other elements provided that the element has a series of holes or similar perforations in order that the element maintains a conductive surface that faces away from the entrance aperture which can be reached by charged particles that have entered the detector. The aperture size of the mesh should not be too fine that the mesh can become completely coated with material so that the ions are not able to pass through to the outwardly facing conductive surface. Generally, thin film coatings will become stressed and then crack once a particular thickness is deposited and will thereafter break off the mesh surface. Thus the mesh size should be chosen to be slightly larger than the maximum thickness of the coating that could otherwise be deposited. In one particular preferred embodiment, a mesh having an aperture of approximately 1 mm was found to provide a useful result.

Figure 6:
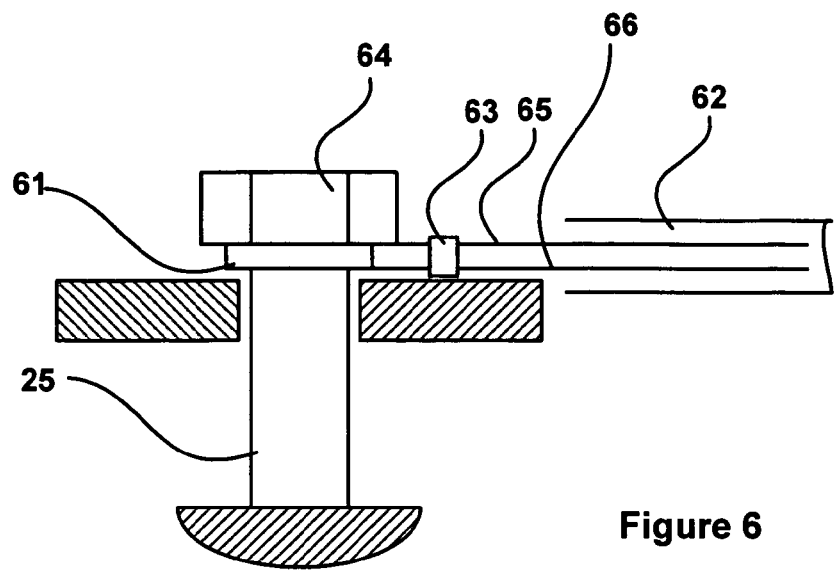
FIG. 6 shows an electrical contact including a thermocouple interface.

FIG. 6 shows the electrical contact for the ion detector. The screw 25 receives a washer 61 to which is connected the signal line 65 which ultimately connects to the control circuit. The washer 61 is retained by a locking nut 64. The signal line 65 includes an outer shield 62 which prevents stray charges from contacting the signal line, thereby effecting the signal.

Figure 7:
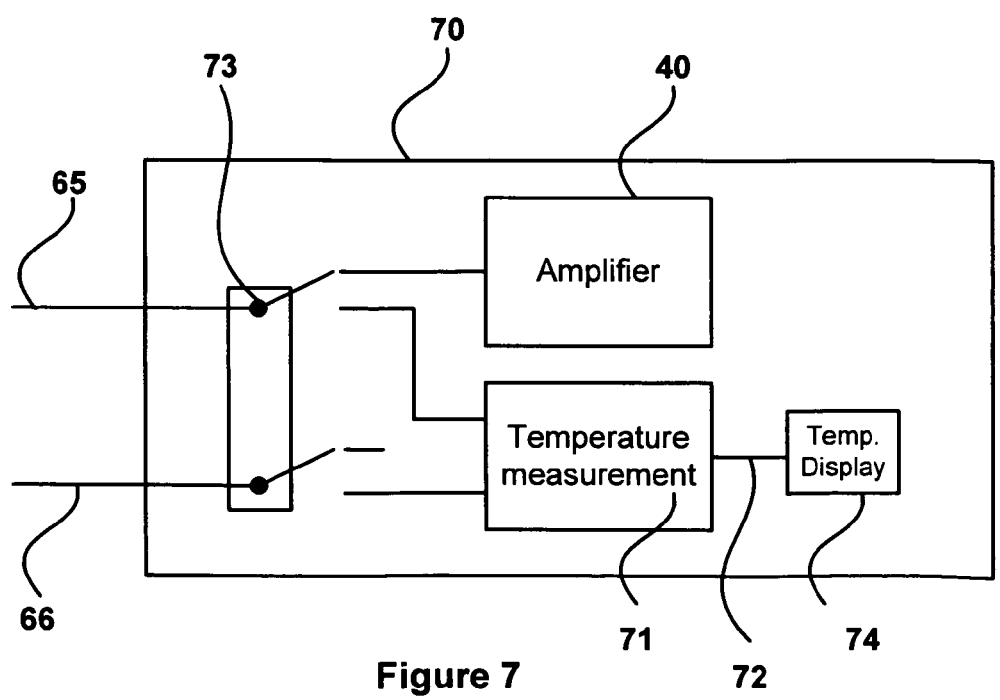
FIG. 7 shows a further example of a control circuit including a temperature sensor display.

In one particularly preferred embodiment, the signal line 62 includes a thermocouple interface 63, such as a Type J interface well known to the skilled addressee, that can measure the temperature of the contact, which will be proportional to the temperature of the detector and the deposition substrate. The interface 63 provides a differential voltage proportional to the temperature across dual strands 65 and 66 of the signal line. Because the ion current and temperature are not able to be measured simultaneously, a modified control circuit as shown in FIG. 7 is used. The circuit 70 includes a double pole switch 73 which switches between the ion current measuring circuit 40 described previously and a temperature measuring circuit 71 which outputs a signal 72 proportional to the temperature to a display 74. In the current detecting mode, signal line 65 connects to the current measuring circuit 40 described previously, whilst signal line 66 terminates. When switching from the ion current measuring circuit 40 to the temperature measuring circuit 71, the bias voltage is removed from the signal line with signal lines 65 and 66 connecting to a differential amplifier circuit 71 which magnifies the differential voltage of the thermocouple interface, as is well known, and outputs a signal to the display to indicate the temperature of the detector.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, and all changes which come within the meaning and range of equivalency are therefore intended to be embraced therein.

I claim:

1. A charge detector including an outer housing including an entrance aperture, the detector further including a charge capture element disposed within said outer housing and electrically isolated from said outer housing, wherein said charge capture element includes a plurality of apertures and a conductive surface facing substantially away from said entrance aperture.

2. A charge detector according to claim 1 further including an electrical contact electrically connected to said conductive surface of said charge capture element and extending from said charge capture element through said housing, said electrical contact being electrically isolated from said housing.

3. A charge detector according to claim 2 further including a signal line extending from said electrical contact for conducting a current signal.

4. A charge detector according to claim 3 wherein the signal line includes at least one inner signal line and an outer electrical shield separated from said at least one inner signal line by an insulator.

5. A charge detector according to claim 3 wherein said signal line is further adapted to conduct a voltage to said detector surface.

6. A charge detector according to claim 1 wherein the housing is includes an electrical contact point.

7. A charge detector system including:
a charge detector including an outer housing including an entrance aperture, a charge capture element disposed within said outer housing, an electrical contact electrically connected to said charge capture element and extending from said charge capture element through said housing, said charge capture element and said electrical contact being electrically isolated from said housing, wherein said charge capture element includes a plurality of apertures and a conductive surface facing substantially away from said entrance aperture; said system further including:
a signal line; and
a control circuit;
wherein the signal line extends from said charge detector to said control circuit, wherein the control circuit is adapted to measure a signal in said signal line and to provide an output signal indicative of a charge captured by said charge capture surface.

8. A charge detector system according to claim 7 wherein the control circuit provides the output signal to a visual display.

9. A charge detector system according to claim 7 wherein the output signal indicative of the charge captured by said charge capture element is a current signal.

10. A charge detector system according to claim 7 wherein the control circuit includes an RMS converter for converting a time varying signal to an RMS signal.

11. A charge detector system according to claim 7 wherein the control circuit includes a bias circuit for providing a bias voltage to said charge capture element.

12. A charge detector system according to claim 11 wherein the bias voltage is provided to the charge capture surface through the signal line.

13. A charge detector system according to claim 7 wherein the control circuit includes a signal amplifier for amplifying the signal received from the charge detector.

14. A charge detector system according to claim 7 further including a temperature sensor, the signal line including at least one line for conducting a temperature indicating signal from said temperature sensor to said control circuitry.

15. A charge detector system according to claim 7 wherein the signal line includes a temperature sensor in thermal contact with said charge detector for measuring the temperature of said charge detector.

16. A charge detector system according to claim 15 wherein the signal line includes a thermocouple at an end of said signal line connected to said charge detector.

17. A charge detector system according to claim 16 wherein the control circuitry includes switching circuitry for switching between a charge measuring mode and a temperature measuring mode.

18. A charge detector system according to claim 17 wherein the control circuitry removes a bias voltage from said signal line during said temperature measuring mode.

* * * * *